(12) United States Patent
Gemen

(10) Patent No.: US 6,338,954 B1
(45) Date of Patent: Jan. 15, 2002

(54) METHOD FOR THE NON-SPECIFIC AMPLIFICATION OF NUCLEIC ACID

(75) Inventor: Bob van Gemen, Almere (NL)

(73) Assignee: PamGene B.V., Den Bosch (NL)

( * ) Notice: Subject to any disclaimer, the term of this patent is extended or adjusted under 35 U.S.C. 154(b) by 0 days.

(21) Appl. No.: 09/623,054

(22) PCT Filed: Jan. 21, 1999

(86) PCT No.: PCT/EP99/00332

§ 371 Date: Aug. 24, 2000

§ 102(e) Date: Aug. 24, 2000

(87) PCT Pub. No.: WO99/43850

PCT Pub. Date: Sep. 2, 1999

(30) Foreign Application Priority Data

Feb. 27, 1998 (EP) .............................................. 98200619

(51) Int. Cl.$^7$ .............................. C12P 19/34; C12Q 1/68
(52) U.S. Cl. .......................................... 435/91.1; 435/6
(58) Field of Search ........................................ 435/91.2

(56) References Cited

U.S. PATENT DOCUMENTS

| | | | | |
|---|---|---|---|---|
| 5,169,766 A | * | 12/1992 | Schuster et al. .............. | 435/91 |
| 5,472,850 A | | 12/1995 | Morrissey ..................... | 435/13 |
| 5,514,545 A | | 5/1996 | Eberwine ....................... | 435/6 |
| 5,545,522 A | | 8/1996 | Van Gelder et al. ............ | 435/6 |
| 5,554,516 A | * | 9/1996 | Kacian et al. ............ | 435/91.21 |

FOREIGN PATENT DOCUMENTS

| | | |
|---|---|---|
| EP | 0 731 174 A2 | 9/1996 |
| FR | 2 724 934 | 3/1996 |
| WO | WO 91/03552 | 3/1991 |
| WO | WO 92/22663 | 12/1992 |
| WO | WO 93/22461 | 11/1993 |
| WO | WO 96/02668 | 2/1996 |
| WO | WO 97/27317 | 7/1997 |

OTHER PUBLICATIONS

Van Gelder R. N. et al., "Amplified RNA synthesized from limited quantities of heterogeneous cDNA", PNAS USA, vol. 87, pp. 1663–1667 (1990).*

Han J. H. et al., "Isolation of Full–Length Putative Rat Lysophospholipase cDNA Using Improved Melthods for mRNA Isolation and cDNA cloning", Biochemistry, vol. 26, pp. 1617–1625 (1987).*

(List continued on next page.)

*Primary Examiner*—Kenneth R. Horlick
*Assistant Examiner*—Teresa Strzelecka
(74) *Attorney, Agent, or Firm*—Nixon & Vanderhye P.C.

(57) ABSTRACT

The present invention is concerned with a method for generating, in a non specific manner, multiple copies of RNA from a pool mRNA's. Such a method is of particular importance in techniques for screening the differences in expression in given cell types or in cells under specific conditions. The present invention provides a non-selective poly A mRNA labeling and amplification method, i.e. a method not encompassing cDNA synthesis. The present invention is directed to a method for amplifying RNA by creating, in a non specific manner, multiple RNA copies starting from nucleic acid containing starting material comprising a pool of mRNA's each mRNA comprising a poly-A tail, wherein the material is contacted simultaneously with an oligonucleotide comprising an oligo-dT sequence, and oligo-dT sequence is blocked at the 3' end, the sequence of a promoter recognized by an RNA polymerase and a transcription initiation region which is located between the oligo-dT sequence and the sequence of the promoter, and further with an enzyme having reverse transcriptase activity, an enzyme having RNase H activity and an enzyme having RNA polymerase activity and the necessary nucleotides and the resulting reaction mixture is maintained under the appropriate conditions for a sufficient amount of time for the enzymatic processes to take place.

22 Claims, 7 Drawing Sheets

OTHER PUBLICATIONS

Kievits et al., "NASBA™ Isothermal Enzymatic in Vitro Nucleic Acid Amplification Optimized for the Diagnosis of HIV-1 Infection," Journal of Virological Methods, vol. 35, No. 3, Dec. 1991, pp. 273–286.

Romano et al., "NASBA a Novel, Isothermal Detection Technology for Qualitative and Quantitative HIV-1 RNA Measurements," Clinics in Laboratory Medicine, vol. 16, No. 1, Mar. 1996, pp. 89–103.

* cited by examiner

SEQUENCE LISTING

<160> NUMBER OF SEQ ID NOS: 1

<210> SEQ ID NO 1
<211> LENGTH: 72
<212> TYPE: DNA
<213> ORGANISM: Artificial Sequence
<220> FEATURE:
<223> OTHER INFORMATION: Description of Artificial Sequence:PRIMER PH26

<400> SEQUENCE: 1
aattctaata cgactcacta tagggagaga aggataccac tagctagcgt tttttttttt        60
tttttttttt tt        72

METHOD FOR THE NON-SPECIFIC AMPLIFICATION OF NUCLEIC ACID

The present invention is concerned with a method for generating, in a non specific manner, multiple copies of RNA from a pool of mRNA's. Such a method is of particular importance in techniques for screening the differences in expression in given cell types or in cells under specific conditions.

In cells of higher organisms only some 15% of the genes present (each cell contains about 100,000 genes) is expressed. Gene expression varies between different cell types and between different stages of development of a given cell and is crucial to all biological processes, such as aging, cell differentiation, and infectious or other disease states. Thus the identification of genes that are differentially expressed in cells under different conditions is of prime interest in cellular biology.

To be able to analyze the mRNA content derived from only a few cells a method is needed to amplify the mRNA present in the cell(s) under investigation. Much effort has already been put in methods to examine the mRNA population of a cell. This has lead to the development of techniques to label nucleic acid material starting from the mRNA population of a cell aimed at the identification of genes that are differentially expressed in cells under various conditions. One method for screening differences in gene expression is a method known as Differential Display (Liang and Pardee, Science, Vol 257, 967–971, 1992; U.S. Pat. No. 5,262,311 which issued on Nov. 16, 1993). With the method of Liang and Pardee mRNA is first transcribed into cDNA and amplified using the Polymerase Chain Reaction (PCR). A set of oligonucleotide primers is used, the first of which is anchored to the polyadenylated tail of a subset of mRNA's, the other being short and arbitrary in sequence so that it anneals at different positions relative to the first primer. The method is used with different pairs of alterable sequences aiming at the amplification of as many mRNA's as possible from the cells under investigation. The PCR products are labeled using tracer amounts of labeled (radioactive) nucleotides.

An improvement on the Differential Display method of Liang and Pardee was disclosed in U.S. Pat. No. 5,589,726. The method described in U.S. Pat. No. 5,589,726 differs from the method of Liang and Pardee in that it uses longer primers (22–30 nucleotides compared to the 9–14 base primers originally described by Liang and Pardee).

Another alleged improvement over the Differential Display technique as originally disclosed by Liang and Pardee is disclosed in WO 97/37045. In this application a method is disclosed that, again, is based on PCR: This method uses an oligo-dT primer rather than an anchored primer. Thus, after the reverse transcription step only one cDNA population covering all possible mRNA sequences is created. The cDNA thus obtained is titrated into the PCR process by running several IPCR reactions at decreasing concentrations of cDNA. This serves to calibrate the method and to protect it against false negatives. The PCR reaction may be performed with anchored primers again.

Yet another method for "expression profiling" of mRNA's is disclosed in U.S. Pat. No. 5,514,545. With this method mRNA in a single cell can be characterized by microinjecting into a cell a first amplification oligonucleotide comprising oligo-dT and the sequence of a bacteriophage promoter such as T7, T3 or SP6, reverse transcriptase and nucleotides to synthesize a first strand of cDNA from the mRNA in the cell. From the first strand of cDNA double stranded cDNA is synthesized. Since this double stranded cDNA includes a functional promoter aRNA (anti-sense RNA) can now be synthesized therefrom using an RNA polymerase. The aRNA is now reamplified using random hexanucleotide primers with a reverse transcriptase to form first strand cDNA.

With all the above techniques cDNA is made starting with a primer using the mRNA as a template. However, the enzyme that is used for this reaction (reverse transcriptase) is hampered in the cDNA synthesis by structures in the mRNA. As a result the prior art methods are selective for mRNA's with little or no structure. This effect is further enhanced if the synthesized cDNA is amplified further, for instance by PCR. Due to the aforementioned it is common practice to use a large sample amount in these type of expression profiling analysis. Thus this technical threshold does not allow the analysis of only a few cells isolated on a cell sorter or a few cells isolated via micro dissection from a glass slide after microscope identification and selection.

The solution to the problem is the use of a non-selective poly A mRNA labeling and amplification method, i.e. a method not encompassing cDNA synthesis.

The present invention provides such a method. The present invention is directed to a method for amplifying RNA by creating, in a non specific manner, multiple RNA copies starting from nucleic acid containing starting material comprising a pool of mRNA's each mRNA comprising a poly-A tail, wherein the material is contacted simultaneously with an oligonucleotide comprising an oligo-dT sequence, the sequence of a promoter recognized by a RNA polymerase and a transcription initiation region which is located between the oligo-dT sequence and the sequence of the promoter, and further with an enzyme having reverse transcriptase activity, an enzyme having RNase H activity and an enzyme having RNA polymerase activity and the necessary nucleotides and the resulting reaction mixture is maintained under the appropriate conditions for a sufficient amount of time for the enzymatic processes to take place.

This will lead to the formation of multiple anti-sense RNA copies of the mRNA's present in the reaction mixture. The method of the present invention does not involve the production of cDNA intermediates; RNA is copied directly from the mRNA present in the material under investigation. The method of the present invention does not need a cDNA as a basis for the amplification of the RNA. The RNA is synthesized by an RNA polymerase, directly from the mRNA template. The activity of the RNA polymerase is independent from any secondary structures present in the mRNA and thus there are no differences in the way the different mRNA's are amplified depending on structures in the mRNA's. The copies made represent the original mRNA population as present in the starting material.

The oligonucleotides used with the method of the invention comprise an oligo-dT sequence which will hybridize to the poly- and enylated tail at the 3' end of the mRNA's. The oligonucleotides further comprise the sequence of a promoter recognized by an RNA polymerase and a transcription initiation region which is located between the oligo-dT sequence and the sequence of the promoter. The promoter may be the promoter for any suitable RNA polymerase. Examples of RNA polymerases are polymerases from *E. coli* and bacteriophages T7, T3 and SP6. Preferably the RNA polymerase is a bacteriophage-derived RNA polymerase, in particular the T7 polymerase.

The oligonucleotide may be blocked at its 3' end. If the oligonucleotide is not blocked at its 3' end, it is extendible by the reverse transcriptase. However, the cDNA that would thus be generated will not be a part of the amplification mechanism (as it is with prior art methods). It even interferes with the other enzymatic reactions. The extension of the oligonucleotide is only with a very limited number of nucleotides because if the promoter is made double stranded the transcription on the mRNA template by the RNA polymerase will start immediately. This transcription will "push" the RT from the RNA template and extension (i.e. cDNA synthesis) of the oligonucleotide can no longer occur. The oligonucleotide can be blocked at its 3' end to prevent any extension therefrom by the reverse transcriptase along the RNA template; the reverse transcriptase will not be able to start extension of the 3' end of the oligonucleotide and no cDNA is synthesized. The reverse transcriptase does synthesize a complementary strand of the promoter sequence present in the template. The use of the oligonucleotide is depicted schematically in FIG. 1. Upon hybridization of the oligonucleotide the poly-A sequence of the mRNA is cut by an enzyme having RNase H activity. This activity may be the RNase H activity of the reverse transcriptase or the RNaseH activity of a separate enzyme like, for example, *E.coli* RNaseH, or both. In that respect preferred transcriptases used with the method of the invention are transcriptases having RNaseH activity, such as AMV-RT or MMLV-RT. The newly generated 3' end of the RNA is extended on the oligonucleotide template to generate a double stranded promoter sequence. By application of the RNA polymerase new RNA copies of the original mRNA are made. During this transcription step labels may be incorporated and typically 100–1000 copies of each RNA are being made. The copies made are antisense RNA and thus comprise a poly-T stretch at the 5' end.

Since the RNA polymerase normally uses a double stranded template for the transcription the enzymes is not likely to be hampered by structures in the mRNA. Furthermore, the processivity of, for example, the T7 RNA polymerase is very high, usually more than 250 nucleotides per second on a DNA template. This means that the amplification rate is determined by the number of initiation events per promoter, per time unit. Since the promoter is identical for each mRNA there is no selectivity in the amplification.

The conditions under which the reaction, should be performed are the normal conditions, i.e. buffer concentrations and temperatures, known to be optimal for the mix of enzymes used.

If the interest exists to make an expression profile of just a few cells the above described amplification may not yield enough copies of the RNA, for example to generate a signal if the copies are labeled. In certain special cases the RNA may need to be amplified further without introducing selectivity, thus again avoiding i.e. cDNA synthesis. There are multiple solutions to this problem, all transcription based. An elegant solution is depicted in FIG. 2. The newly synthesized RNA may now be further amplified by the following method. To the 3' end of every RNA molecule a double stranded promoter sequence is ligated by using RNA ligase. Since all 3' ends are chemically identical there is no selectivity. The ligated promoter is used to initiate a second round of transcription generating more (labeled) RNA. This is illustrated in FIG. 2.

Thus in a preferred method of the invention the generated RNA copies made as described above are contacted with an RNA ligase, a double stranded nucleic acid complex comprising a double stranded DNA promoter sequence that can be recognized by a RNA polymerase, whereby one strand of said complex has a stretch of RNA attached to the 5' end of one of the DNA strands, an enzyme having RNA polymerase activity, and the necessary nucleotides. The resulting reaction mixture is maintained under the appropriate conditions for a sufficient amount of time for the amplification to take place Again, one or more of the nucleotides used may be labeled. Due to the orientation of the RNA polymerase promoter sequence the RNA template is used to generate new sense strand RNA molecules. Typically 100–1000 copies of each RNA is being made in the transcription reaction by the RNA polymerase.

Preferably the stretch of RNA attached to the 5' end of one of the DNA strands is phosphorylated at the 5' end. Phosporylation enables the 5' end to be ligated.

The promoter may be the same as in the first part of the procedure for example, the T7-promoter sequence may be used and the RNA polymerase than is T7 RNA polymerase.

Interestingly the sense RNA made in this second round of transcription contains again a poly A stretch at the 3' end making is possible to perform multiple cycles of amplification by repeatedly performing the method as illustrated by FIG. 1 and the method using the ligase as illustrated in FIG. 2.

The procedure wherein the ligase is used may be performed as a separate reaction. That is, after RNA copies have been generated in a procedure like the one depicted in FIG. 1, the RNA copies may be transferred to another reaction medium and subjected to the second reaction.

When all enzymes and the oligonucleotide and the promoter construct are combined with the initial reaction mixture a continuous process may even be obtained.

Another elegant method to further enhance the amplification factor of the non-biased mRNA amplification method is by adding a poly A nucleotide stretch to the 3' end of the newly synthesized RNA. The poly nucleotide stretch is added by the enzyme poly A polymerase. To this added poly A sequence, the oligonucleotide, encompassing an oligo T stretch and T7 promoter, can hybridize again and the previously described process may take place again. As a result again RNA will be made by the transcription process and this newly synthesized RNA will be identical (for the large part) to the original mRNA that the whole reaction started with in the first place. One skilled in the art understands that the oligonucleotide, encompassing an oligo T stretch and T7 promoter can also hybridize again to this RNA and t he process may be considered a continuous process of RNA synthesis by transcription, oligonucleotide annealing and double strand promoter synthesis.

Thus in a preferred method of the invention the generated RNA copies made as described before in the basic method are contacted with a poly A polymerase, an oligonucleotide, encompassing an oligo T stretch and T7 promoter, a reverse transcriptase, a RNase H, a RNA polymerase and the necessary nucleotides. The resulting reaction mixture is maintained under appropriate conditions for a sufficient amount of time for the amplification to take place. In the mix one or more nucleotides used may be labeled.

Due to the position of the newly added poly A stretch (3' end of the RNA molecules) the RNA polymerase will generate RNA of the opposite polarity. The oligonucleotide, encompassing an oligo T stretch and T7 promoter may be the same as in the first part of the procedure.

The procedure in which the poly A polymerase is added may be performed as a separate reaction. That is, after RNA copies have been made in a procedure like the one depicted in FIG. 1, the RNA copies may be transferred to another reaction medium and subjected to the reaction with poly A polymerase; starting a continuous amplification process.

When the poly A polymerase is added to the initial reaction mixture the continuous amplification process may even start immediately from the original mRNA template.

Figure 4:
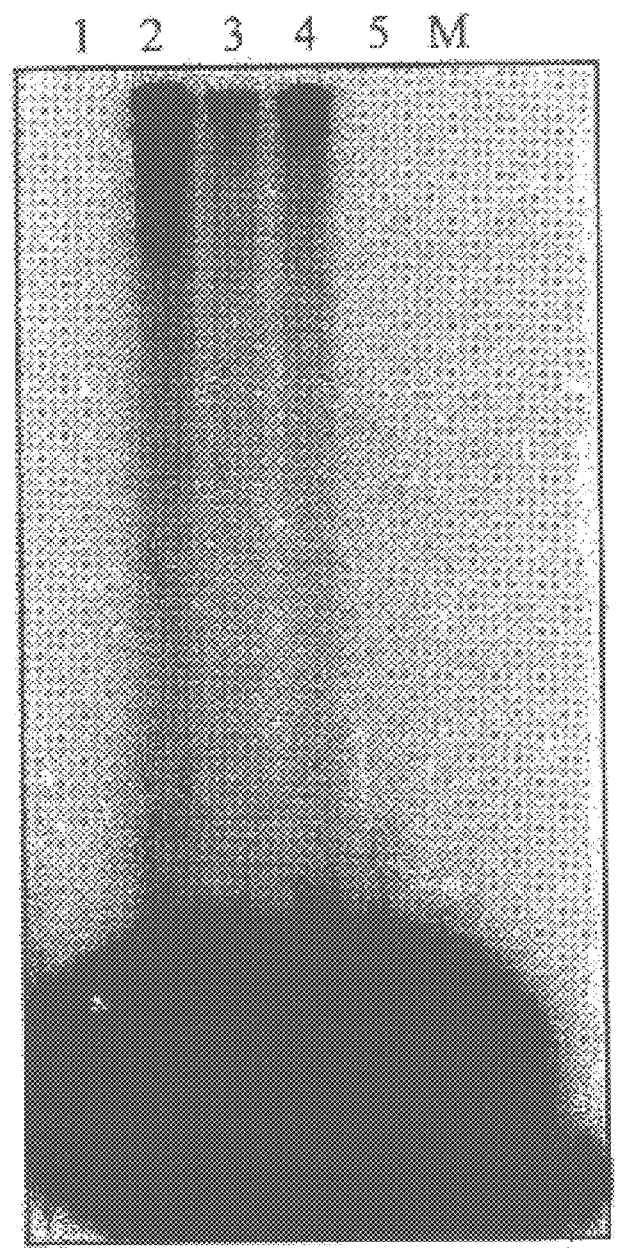

1) 50×dilution
2) 100×dilution
3) 500×dilution
4) 1000×dilution
5) no template
M) 100–400 nt marker
i) input FIG. 4. Autoradiograph of Cleangel showing the radiolabeled Tyras amplification products. Lane 1, input poly A+ RNA; lane 2, 5 minute labeling; lane 3, 10 minute labeling; lane 4, 20 minute labeling; lane 5, no template reaction; lane M, non-labeled marker.

Figure 5:
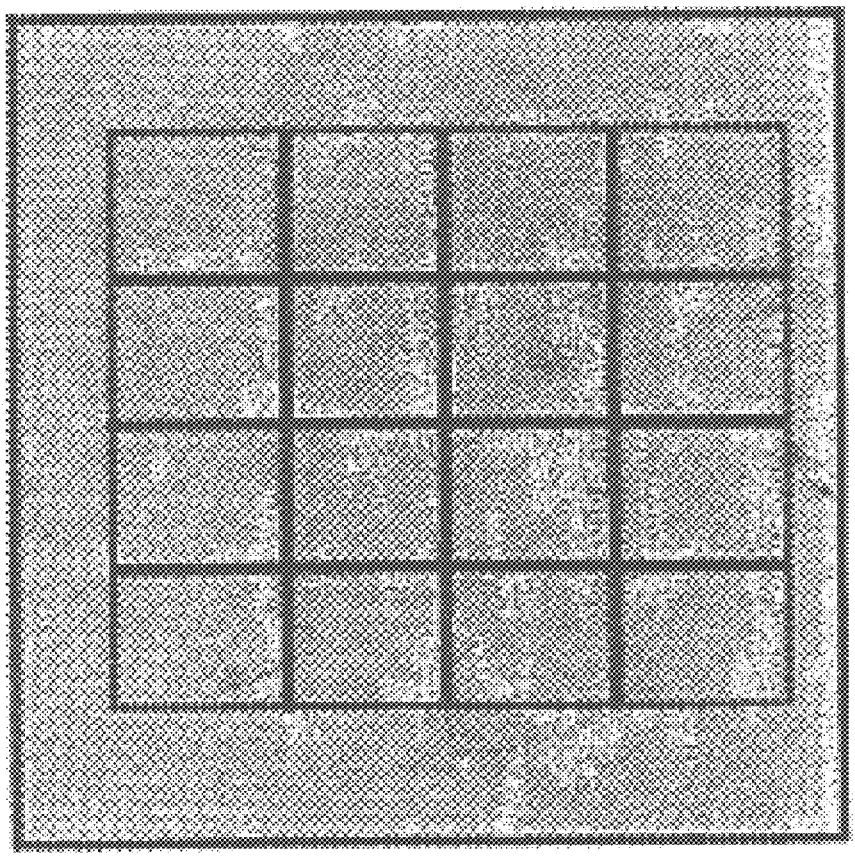

FIG. 5. Autoradiograph of the probe array filer described in table 1 interrogated with the Tyras reaction mixture of example 3.

Figure 6:
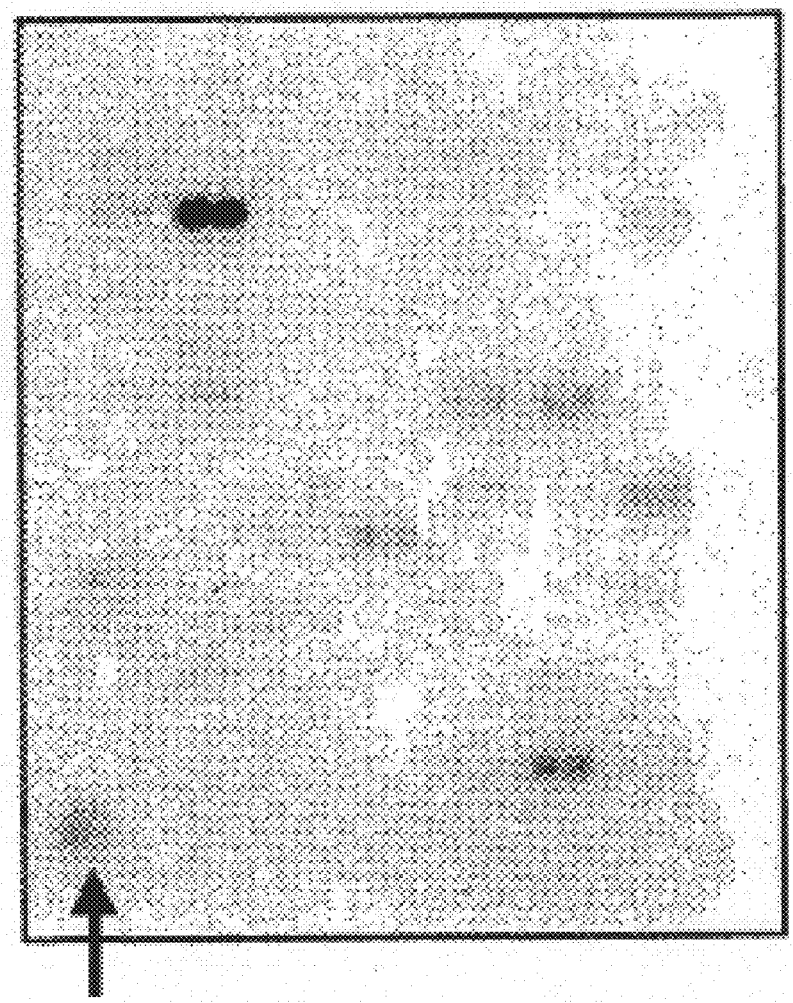

FIG. 6. Autoradiograph of the filter with the "E quadrant" of an Atlas Human cDNA Expression Array. The visible spots dearly indicate hybridization of labeled poly A+ RNA by Tyras. The arrow points to a control spot of G3PDH probe OT1446 that was also positive in example 4 (see FIG. 5).

Figure 7:
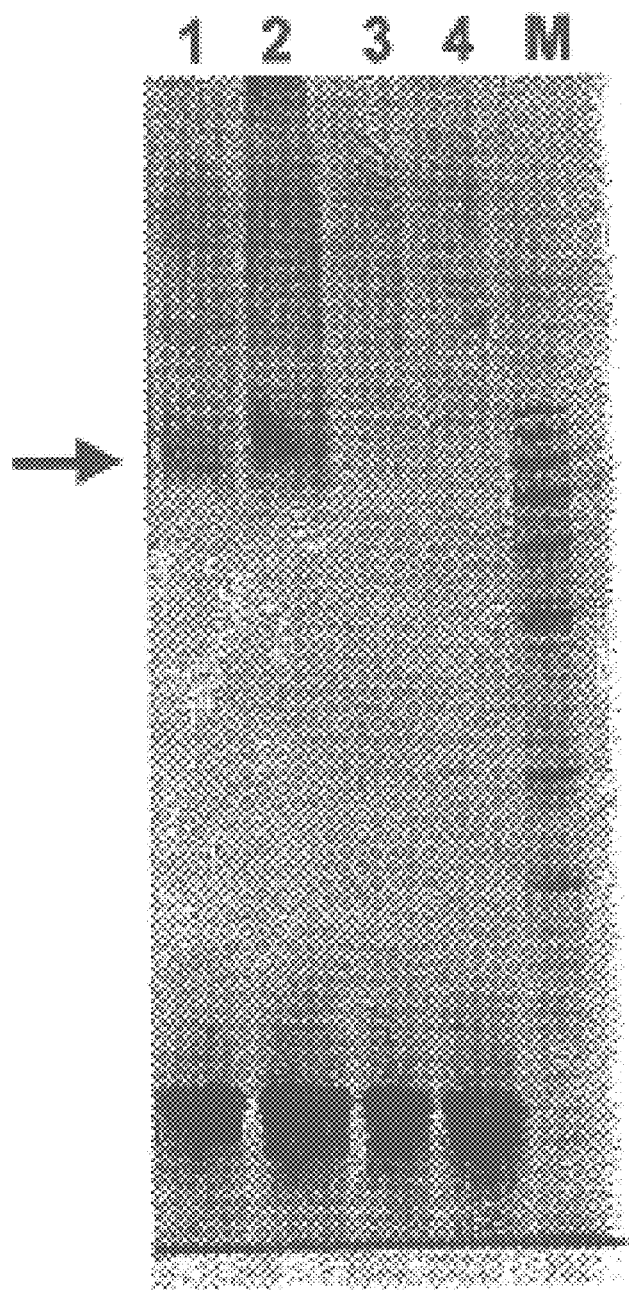

FIG. 7. Silver stained Cleangel analysis of Tyras reactions using the poly A polymerase added poly A tail as target for hybridization of the T stretch encompassing oligonucleotide.

Lane 1, Tyras reaction using 5 microliter of reaction A as input lane 2, Tyras reaction using 5 microliter of reaction B as input; lane 3 and lane 4, negative control lanes; M is marker lane. The arrow indicates the position of the specific amplification product.

EXAMPLES

Introduction

Figure 1:
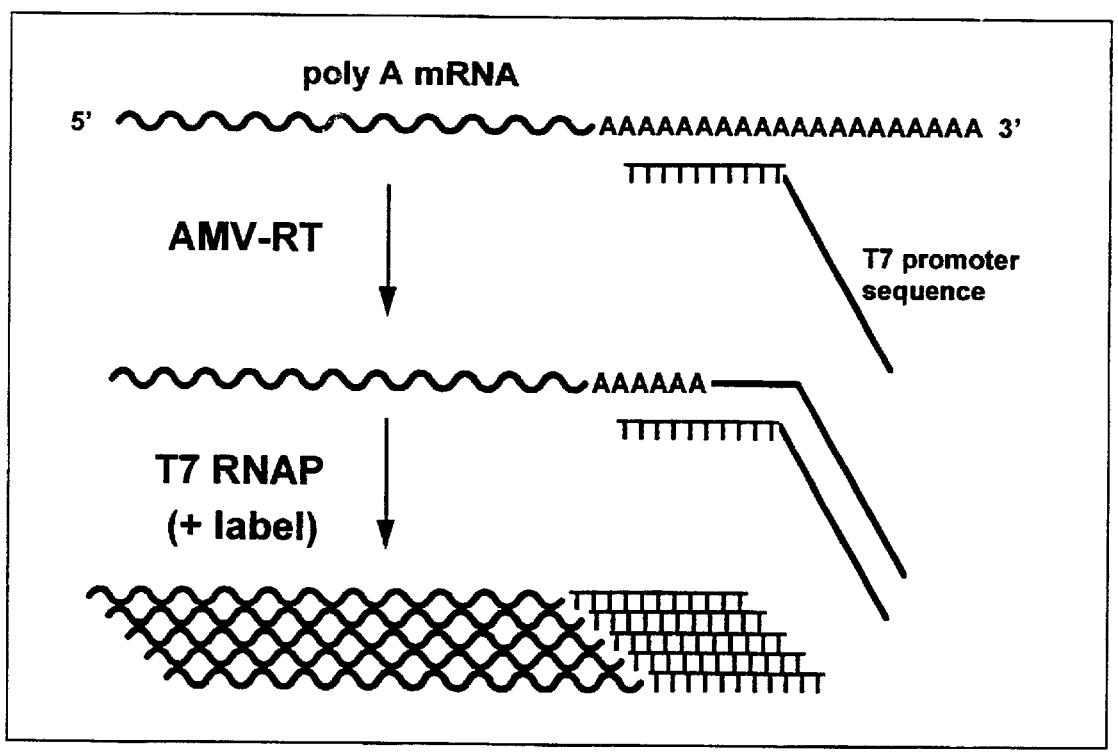
FIG. 1. Schematic presentation of non-selective poly A mRNA amplification based on transcription. RNase H activity necessary for cutting the RNA can be associated with the AMV-RT.
Figure 2:
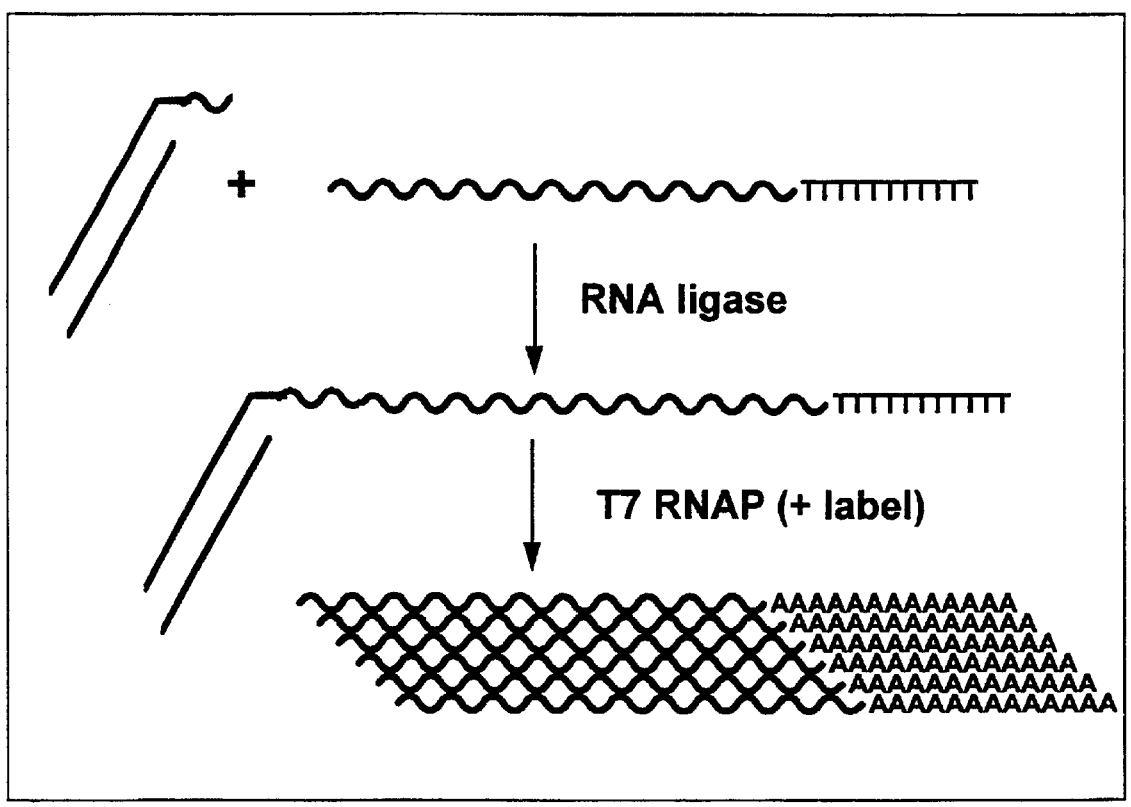
FIG. 2. Schematic presentation of the second round of non-selective amplification of the RNA products resulting from the first described non-selective amplification scheme (such as the one depicted in FIG. 1).

The method used in the examples is an embodiment of the method of the invention and referred to in the examples as "Tyras". The method referred to as Tyras comprises the hybridization of an oligonucleotide, encompassing an oligo T stretch, to the poly A tail of the mRNA followed by RNase H digestion opposite the oligonucleotide and extension of the newly formed 3' end of the mRNA with reverse transcriptase. In this way the T7 RNA polymerase recognition sequence (i.e. T7 promoter) that is part of the oligonucleotide encompassing an oligo T stretch is made double stranded. Upon binding of the T7 RNA polymerase to the promoter the original mRNA molecules are transcribed in multiple RNA copies of the opposite polarity (see FIG. 1).

Materials

Most enzymes, radiolabeled nucleotides, acrylamide Cleangels and oligonucleotides were purchased from Amersham Pharmacia, Bergrand 230, 4707 AT Roosendaal, The Netherlands. AMV-reverse transcriptase was purchased from Seiagaku, Rockville, Md. 120248, USA. Human poly A+ RNA was purchased from ClonTech/Westburg, PO Box 214, 3830 AE Leiden, The Netherlands.

Example 1

Plasmid pG30 containing part of the genomic hepatitis B virus (HBV) sequence (nucteotide numbers 1662–1914, reference: Lai, M. E et al. (1991). Sequence analysis of hepatitis B virus genome of a new mutant of ayw subtype isolated in Sardinia Nucleic Acids Res. 19 (18), 5078) cloned in the Eco RI site behind the T7 promoter was used to generate in vitro transcribed RNA containing a poly A stretch (25 nts) adjacent to the HBV sequence (nucleotide numbers 1662–1914). The plasmid pG30 was digested with restriction enzyme Hind II according to a standard protocol as known by persons skilled in the art The linearized plasmid was transcribed in a standard T7 RNA polymerase in vitro transcription reaction (composition: tris-HCl 40 mM, pH=7.5, $MgCl_2$ 6 mM, spermidine 2 mM, NaCl 10 mM, DTT 10 mM, rNTP's 0.5 mM each, RNA Guard 20 units and 46.5 units T7 RNA polymerase) for 3 hours at 37° C. The length of the in vitro transcribed RNA is 306 nudeotidies. The in vitro transcribed RNA was DNase I treated (1 µl, 10 units) for 30 minutes at 37° C. Following the DNase I treatment the in vitro transcribed RNA was phenol/chloroform purified and ethanol precipitated with standard protocols known to persons skilled in the art. The pelleted in vitro transcribed RNA was dissolved in 20 µl water and dilutions in water used for subsequent experiments.

Example 2

The in vitro transcribed RNA (APPROXIMATELY 1 µg/µl) generated in example 1 was used as template to generate new RNA in a Tyras reaction. The in vitro transcribed RNA from example 1 was diluted 50, 100, 500 and 1000 times, respectively, in water. The Tyras reactions contained: 2 µl water, 4 µl 5×NN buffer (Tris-HCl 200 mM, pH 8.5, MgCl2 60 mM, KCL 350 mM, DTT 25 mM, dNTP's 5 mM each, rATP 10 mM, rUTP 10 mM, rCTP 10 mM, rGTP 7.5 mM, ITP 2.5 mM), 4 µl primer mix (76.9 µl 100% DMSO, 11.6 µl oligonucleotide PH26 [42.9 µM, sequence 5' AAT TCT AAT ACG ACT CAC TAT AGG GAG AGA AGG ATA CCA CTA GCT AGC GTT TTT TTT TTT TTT TTT TTT TTT (SEQ ID NO:1) 3'-biotin] and 11.5 µl water for total volume of. 100 µl) and 5 µl of the appropriate dilution of in vitro transcribed RNA from example 1. The reaction was incubated at 65° C. for 5 minutes and subsequently at 41° C. for 5 minutes. Than 5 µl enzyme mix (sorbitol 1.5M, BSA 2.1 µg, RNase H 0.08 units, T7 RNA polymerase 32 units and AMV-Reverse Transcriptase 25.3 units) was added to the reaction and gently mixed by tapping the tube. After a short incubation of 5 minutes at 41° C. the tubes were briefly spun in a centrifuge to collect all the droplets on the bottom of the tube. The reactions were then incubated for 90 minutes at 41° C. After the reaction the tubes were stored at –20° C.

Figure 3:
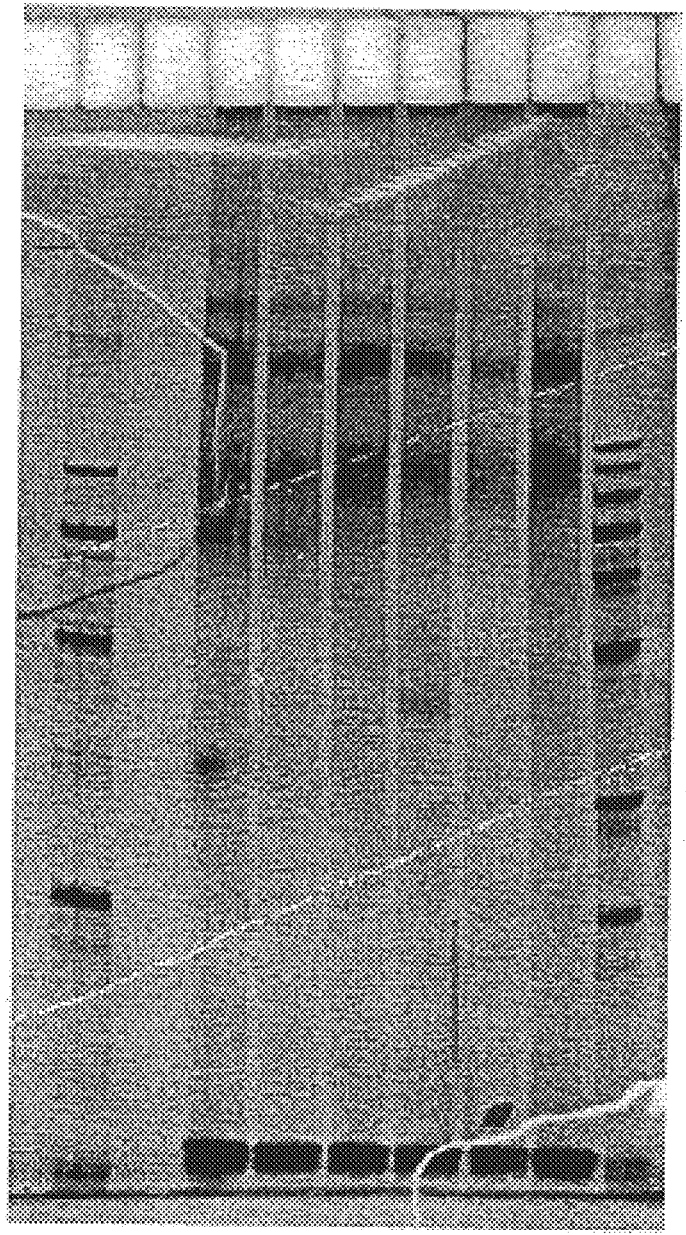
FIG. 3. Silver stained Cleangel analysis of Tyras reactions using different dilutions of in vitro transcribed RNA form example 1 as template.

The reactions were analyzed on a 10% acrylamide Cleangel, wherein 0.5 µl of the Tyras reaction was mixed with 7.5 µl formamide loading dye (Ambion, 2130 woodward St. #200, Austin, Tex. 78744-1832, USA) and run on the Cleangel according to the manufacturers protocol. The result is depicted in FIG. 3.

Example 3

In this example the Tyras reaction was used to generate $^{32}P$ radiolabeled RNA from human placenta poly A+ RNA template. The Tyras reaction contained 4 μl 5×NN* buffer (Tris-HCl 200 mM, pH 8.5, MgCl2 60 mM, KCL 350 mM, DTT 25 mM, dNTP's 5 mM each, rGTP 10 mM, rUTP 10 mM, rCTP 10 mM), 4 μl primer mix PH26 (see example 2), 6.5 μl α-$^{32}$P-ATP and 0.5 μl human poly A+ RNA (1 μg/μl, Clontech lot NR. 7050106, Cat6518-1). The ingredients were mixed tapping the tube and incubated at 65° C. for 5 minutes and subsequently at 41° C. for 5 minutes. Thee 5 μl enzyme mix (sorbitol 1.5M, BSA 2.1 μg, RNase H 0.08 units, T7 RNA polymerase 32 units and AMV-Reverse Transcriptase 25.3 units) was added to the reaction and gently mixed by tapping the tube. After a short incubation of 5 minutes 41° C. the tubes were briefly spun in centrifuge to collect all the droplets on the bottom of the tube. In three tubes labeled A, B and C, respectively, 0.4 μl rATP (100 mM) was added after 0, 5 and 15 minutes incubation at 41° C., respectively. After the addition of the rATP the reactions were incubated for 90 minutes at 41° C. After the reaction the tubes were stored at −20° C.

The reactions were analyzed on a 10% acrylamide Cleangel, 0.5 μl of the Tyras reaction was mixed with 7.5 μl formamide loading dye (Ambion) and run on the Cleangel according to the manufacturers protocol. The result is depicted in FIG. 4.

Example 4

The Tyras reactions of example 3 were pooled and used to interrogate a filter probe array. The composition of the probe array is shown in table 1, the oligonucleotides were spotted on a zeta-probe membrane (BioRad Laboratories, 2000 Alfred Nobel Drive, Hercules, Calif. 94547, USA).

The pooled Tyras reactions from example 3, in total 58.5 μl were added to 25 ml hybridization mix (5×SSC [20×SSC is NaCl 3M, Na-citrate0.3M], 7%, SDS, 20 mM NaPi, 10×Denhardts [100×Denhardts is Polyvinylpyrolidone 2%, BSA 2% and Ficol 2%]). The filter with the probe array was incubated in the hybridization mix for 16 hours (O/N) in a shaking incubator at 42° C.

TABLE 1

Composition of the oligonucleotide probe array interrogated with the labeled Tyras reactions of example 3.

| gamma-actin<br>(+)probe:OT858 | gamma-actin<br>(+)probe:OT85B | gamma-actin<br>(+)probe:OT859 | gamma-actin<br>(+)probe:<br>OT859 |
|---|---|---|---|
| 3.0^13 molecules | 6.0^11 molecules | 3.0^13 molecules | 6.0^11 molecules |
| gamma-actin<br>(+)probe:OT860 | gamma-actin<br>(+)probe:OT860 | G3PDH<br>P2: OT1446 | G3PDH<br>P2: OT1446 |
| 3.0^13 molecules | 6.0^11 molecules | 3.0^13 molecules | 6.0^11 molecules |
| G3PDH<br>P2: OT1447 | G3PDH<br>P2: OT1447 | G3PDH<br>P2: OT1448 | G3PDH<br>P2: OT1448 |
| 3.0^13 molecules | 6.0^11 molecules | 3.0^13 molecules | 6.0^11 molecules |
| Factor V<br>P1: OT1915 | Factor V<br>P1: OT1915 | | |
| 3.0^13 molecules | 6.0^11 molecules | | |

The probe array filter was washed two times in 3×SSC/1% SDS for 7 minutes at room temperature. After the washes the damp filter was wrapped in foil and exposed to an X-ray film O/N at −70° C. The result of the exposure is shown in FIG. 5. The autoradiograph clearly shows a positive signal at the position of the G3PDH probe OT1446 on the array.

Example 5

In this example the Tyras reaction was used to generate $^{32}$P radiolabeled RNA from human poly A+ RNA template.

The Tyras reaction contained 4 μl 5×NN*buffer (Tris-HCl 200 mM, pH 8.5, MgCl2 60 mM, KCL 350 mM, DTT 25 mM, dNTP's 5 mM each, rGTP 10 mM, rUTP 10 mM, rCTP 10 mM), 4 μl primer mix PH26 (see example 2), 6.5 μl α-$^{32}$P-ATP (reactions A and B) or 5.5 μl α-$^{32}$P-ATP (reactions D, E and C) and 0.5 μl human poly A+ RNA (Clontech lot NR. 7050106, Cat.6518-1), in reaction C only water was added since this was the negative control. The ingredients were mixed by pipetting up and down 5 times and incubated at 65° C. for 5 minutes and subsequently at 41° C. for 5 minutes. Than 5 μl enzyme mix (sorbitol 1.5M, BSA 2.1 μg, RNase H 0.08 units, T7 RNA polymerase 32 units and AMV-Reverse Transcriptase 25.3 units) was added to the reaction and gently mixed by tapping the tube. To reaction C, D and E 1 μl of T7 mix (31 units T7 RNA polymerase and 0.6 units RNase H) was added and gently mixed by tapping the tube. After a short incubation of 5 minutes 41° C. the tubes were briefly spun in centrifuge to collect all the droplets; on the bottom of the tube. In all tubes 0.4 μl rATP (100 mM) was added. After the addition of the rATP the reactions A and B were incubated for 90 minutes at 41° C. and reaction C, D and E for 150 minutes at 41° C. After the reaction the tubes were stored at −20° C. The reactions A, B and D were pooled and used to interrogate the "E quadrant" of an Atlas Human cDNA Expression Array (Clontech Laboratories, 1020 East Meadow Circle, Palo Alto, Calif. 94303-4230, USA, lot number 7090625). The filter with the "E quadrant" of an Atlas Human cDNA Expression Array was incubated in hybridization mix (see example 4) for 15 minutes at 50° C. The pooled reactions A, B and D were added to the hybridization mix on the filter and further incubated for 16 hours (O/N). After the hybridization the filter with "E quadrant" of an Atlas Human cDNA Expression Array was washed 4 times with 3×SSC/1% SDS at room temperature. The damp filter was wrapped in foil and exposed to an X-ray film at −70° C. for 65 hours. The result is depicted in FIG. 6 below and dearly shows positive spots on the array indicating good labeling of the poly A+ RNA with the Tyras method.

Example 6

In this example the addition of poly A polymerase to enhance the amplification of the Tyras reaction was investigated. The reaction consisted of model RNA not containing a poly A tail (see also example 1) ATP 1 mM, tris 50 mM, pH=7.9, NaCl 250 mM, MgCl$_2$ 10 mM, BSA 2.5 mg/ml and poly A polymerase (Gibco BRL, catalogue number 18032-011) 1.3 units in a total volume of 30 μl. The reactions were incubated at 37° C. for 20 minutes (reaction A) or 60 minutes (reaction B). Subsequently the products of the reaction that now have a newly added poly A stretch to the 3' end were used in a Tyras reaction as described in example 2. After the 90-minute incubation at 41° C. the Tyras reaction products were analyzed on a 10% acrylamide Cleangel. For loading on the gel 0.5 μl of the Tyras reaction was mixed with 7.5 μl formamide loading dye (Ambion, 2130 woodward St. #200, Austin, Tex. 78744-1832, USA) and run on the Cleangel according to the manufacturers protocol. The result is depicted in FIG. 7.

Although many of the visible bands on the gel seem to be the result of ingredients in the reaction (see lane 3 and 4) at the position of the arrow a specific band can be observed in lanes 1 and 2. This result clearly indicates that it is possible to add a poly A stretch to RNA and subsequently use this newly added poly Ak stretch as start for the Tyras amplification.

What is claimed is:

1. A method for creating, in a non-specific manner, multiple RNA copies, comprising the steps of:

contacting a nucleic acid containing starting material comprising a pool of mRNAs, wherein said mRNAs comprise a poly-A tail, with i) an oligonucleotide containing a 5' end and a 3' end, said oligonucleotide comprising an oligo-dT sequence at said 3' end, a promoter sequence recognized by a RNA polymerase at said 5' end and a transcription initiation region located between the oligo-dT sequence and the promoter sequence, wherein the oligonucleotide is blocked at said 3' end such that extension therefrom is prohibited, ii) an enzyme having reverse transcription activity which forms a double stranded promoter-primer sequence, iii) at least one enzyme having RNase H activity, iv) an enzyme having RNA polymerase activity, and v) sufficient amounts of dNTPs and rNTPs, and maintaining the resulting reaction mixture under appropriate conditions for a sufficient amount of time for the enzymatic processes to occur, such that antisense RNA is formed in the absence of cDNA intermediates.

2. The method according to claim 1, wherein the promoter sequence is the T7-promoter sequence and the RNA polymerase is T7 RNA polymerase.

3. The method according to claim 1, wherein the enzyme having reverse transcriptase activity is AMV-RT or MMLV-RT.

4. The method according to claim 1, wherein said at least one enzyme having RNase H activity is an *E. coli* RNase H.

5. The method according to claim 1, wherein the enzyme having RNase H activity is a reverse transcriptase.

6. The method according to claim 5, wherein the enzyme having RNase H activity is AMV-RT or MMLV-RT.

7. The method according to claim 1, wherein at least one of the dNTPs and rNTPs is provided with a label.

8. The method according to claim 1, wherein the RNA copies are used as input material for further amplification.

9. The method according to claim 8, wherein the RNA copies are contacted with i) a RNA ligase, ii) a double stranded DNA complex comprising a double stranded DNA promoter sequence, wherein each strand contains a 5' end and a 3' end, said promoter sequence being capable of being recognized by a RNA polymerase, wherein one strand of said complex has a stretch of RNA attached to the 5' end thereof, iii) an enzyme having RNA polymerase activity, and iv) sufficient amounts of dNTPs and rNTPs, and maintaining the resulting reaction mixture under appropriate conditions for a sufficient amount of time for the enzymatic processes to occur.

10. The method according to claim 9, wherein the stretch of RNA attached to the 5' end of one of the DNA strands is phosphorylated at the 5' end.

11. The method according to claim 10, wherein the promoter sequence is the T7-promoter sequence and the RNA polymerase is T7 RNA polymerase.

12. The method according to claim 10, wherein at least one of the dNTP's and rNTP's is provided with a label.

13. The method according to claim 1, wherein the reaction mixture further comprises an RNA ligase and a double stranded DNA complex comprising a double stranded DNA promoter sequence that can be recognized by the RNA polymerase, wherein one strand of said complex has a stretch of RNA attached to the 5' end thereof.

14. The method according to claim 1, wherein the RNA copies are contacted with a poly A polymerase.

15. A method for creating, in a non-specific manner, multiple RNA copies, comprising the steps of:

contacting a nucleic acid containing starting material comprising a pool of mRNAs, wherein said mRNAs comprise a poly-A tail, with i) an oligonucleotide containing a 5' end and a 3' end, said oligonucleotide comprising an oligo-dt sequence at said 3' end, a promoter sequence recognized by a RNA polymerase at said 5' end and a transcription initiation region located between the oligo-dt sequence and the promoter sequence, wherein The oligonucleotide is blocked at said 3' end such that extension therefrom is prohibited, ii) an enzyme having reverse transcription activity which forms a double stranded promoter-primer sequence, iii) at least one enzyme having RNase H activity, iv) an enzyme having RNA polymerase activity, v) a poly A polymerase and vi) sufficient amounts of dNTPs and rNTPs, and maintaining the resulting reaction mixture under appropriate conditions for a sufficient amount of time for the enzymatic processes to occur.

16. The method according to claim 15, wherein the promoter sequence is the T7-promoter sequence and the RNA polymerase is T7 RNA polymerase.

17. The method according to claim 15, wherein the enzyme having reverse transcriptase activity is AMV-RT or MMLV-RT.

18. The method according to claim 15, wherein said at least one enzymes having RNase H activity is *E. coli* RNase H.

19. The method according to claim 15, wherein the enzyme having RNase H activity is a reverse transcriptase.

20. The method according to claim 19, wherein the enzyme having RNase H activity is AMV-RT or MMLV-RT.

21. The method according to claim 15, wherein at least one of the dNTP's and rNTP's is provided with a label.

22. The method according to claim 15, wherein the RNA copies are used as input material for further amplification.

* * * * *